United States Patent
Shanmuganathan

(10) Patent No.: US 11,657,570 B2
(45) Date of Patent: May 23, 2023

(54) CREATING A 3D MODEL USING TWO OR MORE CAMERAS WITH VARIABLE FOCAL LENGTHS

(71) Applicant: KONINKLIJKE PHILIPS N.V., Eindhoven (NL)

(72) Inventor: Praveen Kumar Pandian Shanmuganathan, Monroeville, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 53 days.

(21) Appl. No.: 17/335,468

(22) Filed: Jun. 1, 2021

(65) Prior Publication Data

US 2021/0375046 A1    Dec. 2, 2021

Related U.S. Application Data

(60) Provisional application No. 63/033,236, filed on Jun. 2, 2020.

(51) Int. Cl.
| | | |
|---|---|---|
| *G06T 17/20* | (2006.01) | |
| *H04N 13/271* | (2018.01) | |
| *A61M 16/06* | (2006.01) | |
| *H04N 13/239* | (2018.01) | |
| *H04N 13/00* | (2018.01) | |

(52) U.S. Cl.
CPC .............. *G06T 17/20* (2013.01); *A61M 16/06* (2013.01); *H04N 13/239* (2018.05); *H04N 13/271* (2018.05); *H04N 2013/0081* (2013.01)

(58) Field of Classification Search
None
See application file for complete search history.

(56) References Cited

U.S. PATENT DOCUMENTS

| | | | |
|---|---|---|---|
| 9,189,857 B2 | 11/2015 | Hwang | |
| 9,204,127 B1* | 12/2015 | Cole | ............... H04N 13/20 |
| 10,297,076 B2 | 5/2019 | Ban | |
| 2019/0026451 A1 | 1/2019 | Tiwari | |
| 2019/0167934 A1* | 6/2019 | Lucey | ............ G06V 40/169 |
| 2019/0184122 A1 | 6/2019 | Baiko | |

FOREIGN PATENT DOCUMENTS

CN          104616288 A        5/2015

OTHER PUBLICATIONS

Masiero, A. et al., "Initial Evaluation of 3D Reconstruction of Close Objects with Smartphone Stereo Vision". The International Archives of the Photogrammetry, Remote Sensing and Spatial Information Sciences, vol. XLII-1, 2018.

* cited by examiner

*Primary Examiner* — Kent W Chang
*Assistant Examiner* — Jonathan M Cofino
(74) *Attorney, Agent, or Firm* — Michael W. Haas

(57) ABSTRACT

A method of creating a 3D model of a physical object includes adaptively and iteratively generating a number disparity maps from image data representing a plurality of images of the physical object iteratively captured by a plurality of cameras having electrically adjustable focal lengths by varying at least one of the focal lengths of the plurality of cameras and a distance of the physical object from the plurality of cameras during capture of the images until one of the disparity maps is determined to have a least a threshold level of disparity, and converting the one of the disparity maps into the 3D model.

11 Claims, 5 Drawing Sheets

CREATING A 3D MODEL USING TWO OR MORE CAMERAS WITH VARIABLE FOCAL LENGTHS

CROSS-REFERENCE TO RELATED APPLICATIONS

This patent application claims the priority benefit under 35 U.S.C. § 119(e) of U.S. Provisional Application No. 63/033,236, filed on Jun. 2, 2020, the contents of which are herein incorporated by reference.

BACKGROUND OF THE INVENTION

1. Field of the Invention

The present invention pertains to a method and apparatus for generating three-dimensional (3D) models (also referred to as 3D objects) of the surfaces of physical objects, such as the faces of individuals, and, in particular, to a method and apparatus for creating a 3D model using images captured by two or more cameras having variable focal lengths. Such a method and apparatus may have applicability in any application that requires a high quality 3D model including, without limitation, the sizing of respiratory patient interface devices, the sizing of other products such as clothing, eyewear, cosmetics. caps, etc., and facial authentication and recognition systems.

2. Description of the Related Art

As is known in the art, a 3D model or 3D object is a mathematical representation of the surface of a physical object in three dimensions. Many applications benefit from or even require the acquisition of high quality 3D models. For example, it is well known to treat sleep disordered breathing by applying a continuous positive air pressure (CPAP) to the patient's airway. It is also known to provide a positive pressure therapy in which the pressure of gas delivered to the patient varies with the patient's breathing cycle, or varies with the patient's breathing effort, to increase the comfort to the patient. The positive pressure effectively "splints" the airway, thereby maintaining an open passage to the lungs.

Such pressure support therapies involve the placement of a patient interface device including a mask component having a soft, flexible sealing cushion on the face of a patient. Proper mask fit, therefore, is an important consideration in such treatment. In order to ensure a proper fit, the three dimensional facial geometry of a patient is often used to determine the mask that will fit best on the face of the patient. In such situations, 3D scanners and cameras may be used to extract the facial geometry and dimensions of the patient. 3D scanners and cameras, however, are expensive, and it may not be practical to provide such equipment where needed. For example, it may not be practical to provide 3D scanners and cameras in clinical settings, such as multiple sleep labs, where mask fitting is performed. Other applications which may utilize high quality 3D models include, without limitation, the sizing of clothing and facial authentication and recognition systems, and, again, in such situations it may not be practical to provide relatively expensive 3D scanners and cameras.

SUMMARY OF THE INVENTION

Accordingly, it is an object of the present invention to provide a method and apparatus for 3D model generation that overcomes the shortcomings of conventional 3D model generation techniques. This object is achieved according to one embodiment of the present invention by providing a method of creating a 3D model of a physical object, wherein the method include adaptively and iteratively generating a number disparity maps from image data representing a plurality of images of the physical object iteratively captured by a plurality of cameras having electrically adjustable focal lengths by varying at least one of the focal lengths of the plurality of cameras and a distance of the physical object from the plurality of cameras during capture of the images until one of the disparity maps is determined to have a least a threshold level of disparity, and converting the one of the disparity maps into the 3D model.

In another embodiment, a method of proposing a number of articles, such as patient interface devices, for a subject, is provided. The method includes creating a 3D model of the subject according of the method just described, selecting the number of articles based on dimensions from the 3D model and stored dimensions of the number of articles, and displaying the number of articles on a display of an electronic device.

In still another embodiment, an apparatus for creating a 3D model of a physical object is provided. The apparatus includes a plurality of cameras having electronically adjustable focal lengths, and a processing unit coupled to the plurality of cameras. The processing unit is structured and configured for: (i) adaptively and iteratively generating a number disparity maps from image data representing a plurality of images of the physical object iteratively captured by the plurality of cameras by varying at least one of the focal lengths of the plurality of cameras and a distance of the physical object from the plurality of cameras during capture of the images until one of the disparity maps is determined to have a least a threshold level of disparity, and (ii) converting the one of the disparity maps into the 3D model.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 2:
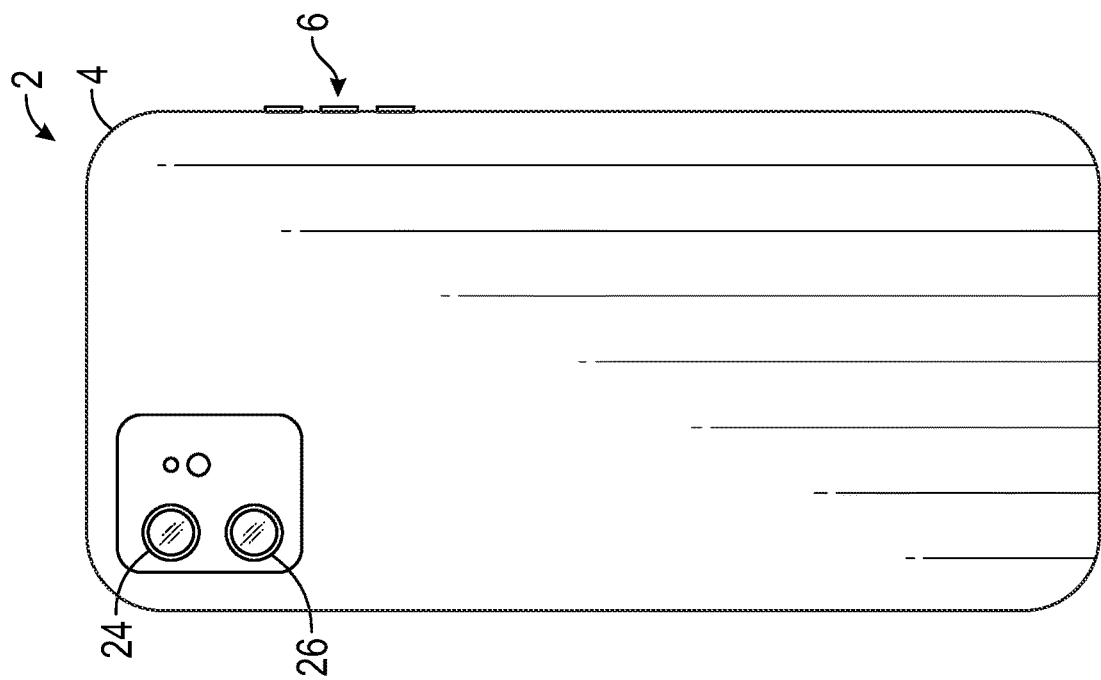
FIG. 2 is a rear elevational view.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As is known in the art, 3D models can be generated using computer stereo vision techniques. In such techniques, 3D information is extracted from two or more digital images, such as those obtained by CCD cameras, by examining the relative positions of objects in the images. For example, it is known that a 3D model can be generated by capturing images from two or more cameras, extracting a disparity map from the captured images, creating a depth map from the disparity map, producing a point cloud from the depth map, converting the point cloud to a polygon mesh, and creating the 3D model from the polygon mesh.

Many smartphones that are available today are provided with a dual rear camera set up that includes cameras of different, electronically adjustable focal lengths. The dual camera set up in such smartphones is primarily used for taking portrait mode pictures, which focus the subject in the scene and blur the background. The disclosed concept provides a method and apparatus that may utilize such dual camera setups to generate 3D models for use in various applications, such as, without limitation, respiratory mask fitting as described elsewhere herein. More specifically, as explained in greater detail herein, the disclosed concept provides a methodology for generating 3D models from images captured by two or more cameras, such as the dual rear cameras in many current smartphones, wherein disparity maps are generated and evaluated for suitability for producing a 3D model prior to proceeding to the other steps of the 3D model generation. If a generated disparity map is determined to not be suitable for 3D model generation (i.e., if it does not meet certain threshold conditions), certain parameters, including one or more of the focal lengths of the cameras and/or the physical position of the object in the scene, can be adjusted in order to produce a more suitable disparity map before proceeding further. The disclosed concept thus improves 3D model generation by adaptively capturing images and creating disparity maps therefrom until a suitable set of images for 3D model production is obtained.

Figure 1:
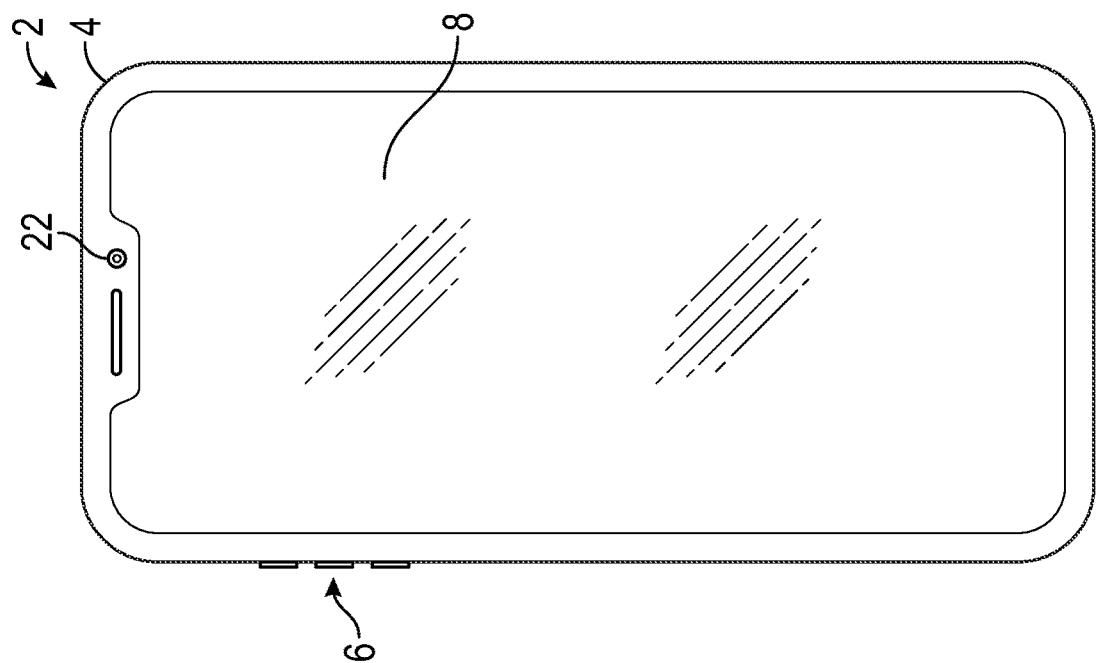
FIG. 1 is a front elevational view.
Figure 3:
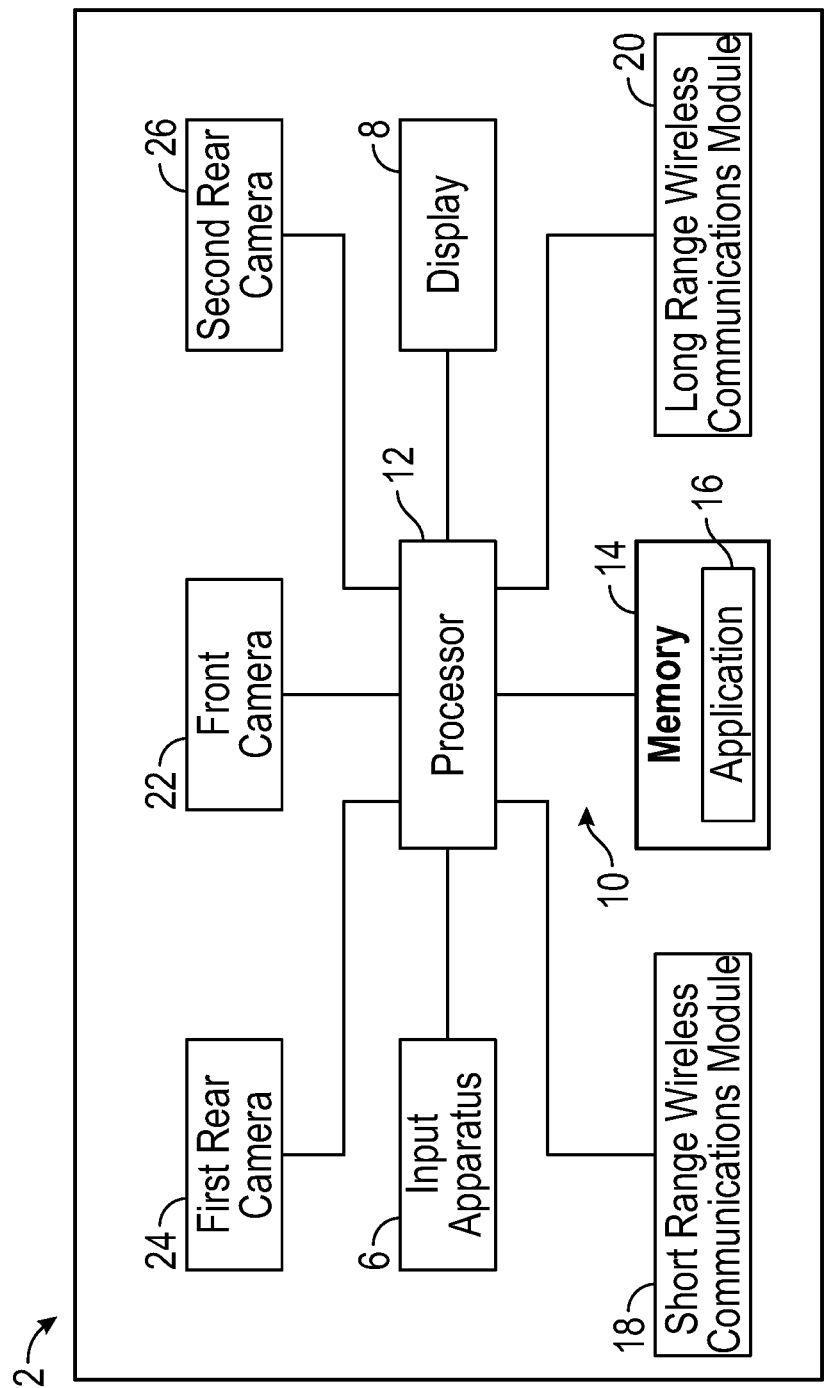
FIG. 3 is a schematic diagram of an apparatus (e.g., a smartphone) which is structured and configured to generate 3D models according to an exemplary embodiment of the disclosed concept.

FIG. 1 is a front elevational view, FIG. 2 is a rear elevational view, and FIG. 3 is a schematic diagram of an apparatus 2 which is structured and configured to generate 3D models according to an exemplary embodiment of the disclosed concept as described herein. The exemplary apparatus 2 depicted in FIGS. 1-3 is, for illustrative purposes, a smartphone, although it will be appreciated that apparatus 2 may be another other type of electronic device, such as, without limitation, a tablet computer, a laptop computer or a PC, without departing from the scope of the disclosed concept. As seen in FIGS. 1-3, apparatus 2 includes a housing 4, an input apparatus 6 (which in the illustrated embodiment is a plurality of buttons), a touchscreen display 8, and a processing apparatus 10 (FIG. 3) disposed in housing 4. A user is able to provide input into processing apparatus 10 using input apparatus 8 and touchscreen display 8. Processing apparatus 10 provides output signals to touchscreen display 8 to enable touchscreen display 8 to display information to the user as described in detail herein.

As seen in FIG. 3, processing apparatus 10 comprises a processor 12 and a memory 14. Processor 12 may be, for example and without limitation, a microprocessor (μP) that interfaces with memory 14, or any other type of processing device, such as a microcontroller or an ASIC. Memory 14 can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 14 has stored therein a number of routines that are executable by processor 12. One or more of the routines implement (by way of computer/processor executable instructions) a software application 16 that is configured to, among other things, generate 3D models according to the methodology of the disclosed concept as described in detail herein in various particular exemplary embodiments. In the exemplary embodiment, application 16 may be downloaded to apparatus 2 from any suitable source, such as an online "app store."

As seen in FIG. 3, apparatus 2 also includes a short range wireless communications module 18 that is structured and configured to enable apparatus 2 to communicate with other, similarly equipped electronic devices over a short range wireless network. In the exemplary embodiment, short range wireless communications module 18 is a Bluetooth® module that that is structured and configured to enable apparatus 2 to communicate with other devices over an ad hoc Bluetooth® network. Apparatus 2 also includes a long range wireless communications module 20 (e.g., a modem) that is structured and configured to enable apparatus 2 to communicate with other electronic devices and systems over a suitable network, such as the Internet.

In addition, apparatus 2 further includes a front camera 22 (e.g., a CCD camera), and first and second rear cameras 24 and 26 (e.g., each a CCD camera). In the exemplary embodiment, the optical focal lengths of each of front camera 22, first rear camera 24, and second rear camera 26 can be electronically adjusted under the control of processing apparatus 10 by, for example, selectively adjusting the sensitivity of the sensing elements of such cameras 22, 24 and 26. In addition, apparatus 2 may also include one or more additional modules and/or components that provide additional functionality. For example, and without limitation, apparatus 2 may include other I/O components, such as, without limitation, a microphone and a speaker.

Figure 4:
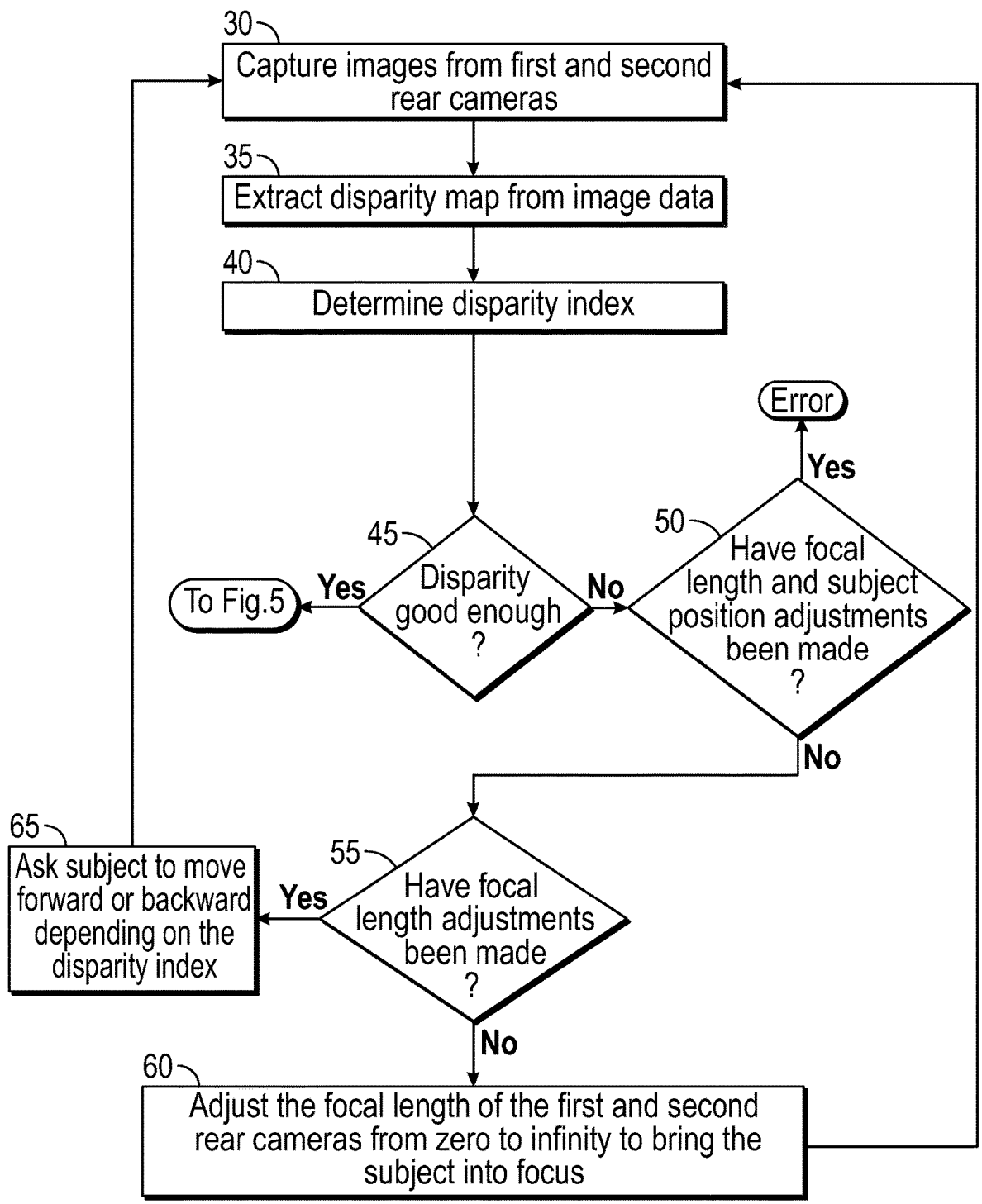
FIGS. 4 and 5 are a flowchart illustrating a method of creating a 3D model using images captured by two or more cameras having variable focal lengths according to an exemplary embodiment of the disclosed concept.
Figure 5:
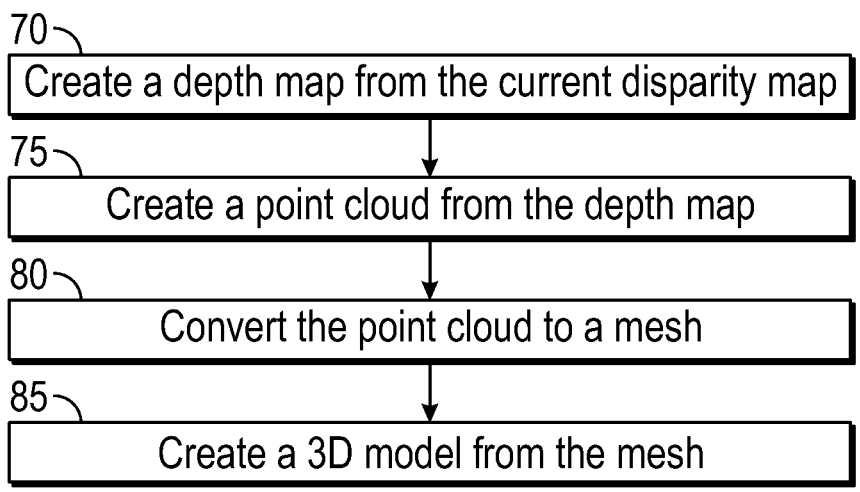

FIGS. 4 and 5 are a flowchart illustrating a method of creating a 3D model using images captured by two or more cameras having variable focal lengths according to an exemplary embodiment of the disclosed concept. For illustrative purposes, the method is described in connection with apparatus 2, and, in particular, is implemented by one or more routines of application 16 that is stored by memory 14 and executable by processor 12. It will be appreciated, however, that this is meant to be exemplary only, and that the method illustrated in FIGS. 4 and 5 can be implemented in connection with other systems and apparatuses.

Referring to FIG. 4, the method begins at step 30, wherein an image of a subject is captured from each of first rear camera 24 and second rear camera 26. Next, at step 35, a disparity map is extracted from the image data of the images captured in step 30. Disparity maps are well known in the art. A disparity map is a way of extracting the depth of a scene from multiple cameras. In particular, it is a representation of pixel differences between multiple cameras in a scene, which can then be used to calculate the depth of the scene. A number of methodologies are known for creating disparity maps from two or more images, any of which may be employed in connection with the disclosed concept.

Next, at step 40, a disparity index is determined for the disparity map extracted in step 35. More specifically, according to an aspect of the disclosed concept, the disparity index is a score that is created from the disparity map and is an aggregate of the individual disparity scores of each of the multiple images (and thus multiple sensors) that are captured in Step 30. The disparity index is thus an indicator of the degree of disparity that is present in the images captured in step 30. If the disparity index is positive, it means the subject has to be moved closer than the original input. If the disparity index is negative, it means that the subject has to be moved farther than the original input. This significance of this fact to the disclosed concept is explained below.

Following step 40, i.e., after the disparity index is determined, the method proceeds to step 45, wherein a determination is made as to whether the disparity of the disparity map (and thus the captured images) is good enough (based on the disparity index) to proceed to the remaining steps of 3D model generation that are described herein. In particular, in step 45, the absolute value of the disparity index that was calculated at step 40 is compared to a predetermined threshold value. In any particular case, the predetermined threshold value will be a function of the image sensors and their tolerances. If the absolute value of the disparity index is greater than the threshold value, then the disparity in the current images is deemed to be good enough to proceed to further 3D model generation. If the absolute value of the disparity index is less than the threshold value, then the disparity in the current images is deemed to not be good enough to proceed to further 3D model generation.

Thus, if the answer at step 45 is yes, then the method proceeds to the steps of FIG. 5, which are the additional steps of 3D model generation (described elsewhere herein). If, however, the answer at step 45 is no, then the method proceeds to step 50. At step 50, a determination is made as to whether focal length and subject position adjustments have already been made according to the disclosed concept (see the description below). If the answer is yes, then an error is indicated, as an appropriate set of images has not been able to be obtained for 3D model generation. However, if the answer at that 50 is no, then the method proceeds to step 55.

At step 55, a determination is made as to whether focal length adjustments according to the disclosed concept have been made. If the answer is no, then the method proceeds to step 60. At step 60, the focal length of the first and second rear cameras 24 and 26 are adjusted from zero to infinity to bring up the subject into focus. Then the method returns to step 30, wherein new images are captured from the first and second rear cameras 24 and 26 for processing according to the disclosed concept as described herein.

If, however, the answer at step 55 is yes, then the method proceeds to step 65. At step 65, the subject is asked to move forward or backward depending upon the determined disparity index. In particular, in the exemplary embodiment, a message is displayed on display 8 of apparatus 2 instructing the subject to move accordingly. In the exemplary embodiment, if the disparity index is positive, then the subject is asked to move closer to apparatus 2. If the disparity index is negative, then the subject is asked to move farther from apparatus 2. Then, the method returns to step 30, wherein new images are captured from the first and second rear cameras 24 and 26 for processing according to the disclosed concept as described herein.

Thus, as will be appreciated from the above description, the method steps shown in FIG. 4 result in the adaptive generation of disparity maps by first varying focal length and then varying subject position until images having disparity suitable for 3D model generation are obtained. As noted above, when such suitable images are obtained, the steps provided in FIG. 4 result in the method proceeding to the steps of FIG. 5, described below.

Referring to FIG. 5, the method steps therein begin at step 70, wherein a depth map is created from the disparity map that has been previously determined to meet the disparity threshold conditions. A depth map is a representation of how close or far different objects are in the scene. A depth map is usually a flattened image representation showing the depth of the objects. A number of methodologies are known in the art for creating depth maps from disparity maps, and any such a suitable methodology may be employed in connection with the disclosed concept. For example, a depth map from the disparity map is often calculated by the formula: Depth Map=baseline*focal length/disparity.

Next, at step 75, a point cloud is created from the depth map. A Point cloud is a three dimensional representation of every point in the scene with their X,Y and Z representations. A number of methodologies are known in the art for creating point clouds from depth maps, and any such suitable methodology may be employed in connection with the disclosure concept. Then, at step 80, the point cloud created in step 75 is converted to a mesh, such as a polygon mesh. As is known in the art, multiple vertices in a point cloud are joined together to create a mesh. A mesh is thus a three dimensional surface representation of a point cloud. In a mesh, multiple vertices from the point cloud are joined together to create triangles and faces. Several triangulation methodologies are known and may be used to convert the point cloud into a mesh in the disclosed concept. Finally, at step 85, a 3D model, which is a standard representation of a mesh, is created from the mesh that was created in step 80.

Thus, the disclosed concept described herein provides a method and apparatus for creating 3D models wherein efforts are made to ensure that images with appropriate disparity, and thus appropriate disparity maps, for creating quality 3D models are obtained before the remaining steps of 3D model generation are initiated. The disclosed concept thus improves the efficiency and quality of 3D model generation for any of a number of applications that utilize 3D models.

Figure 6:
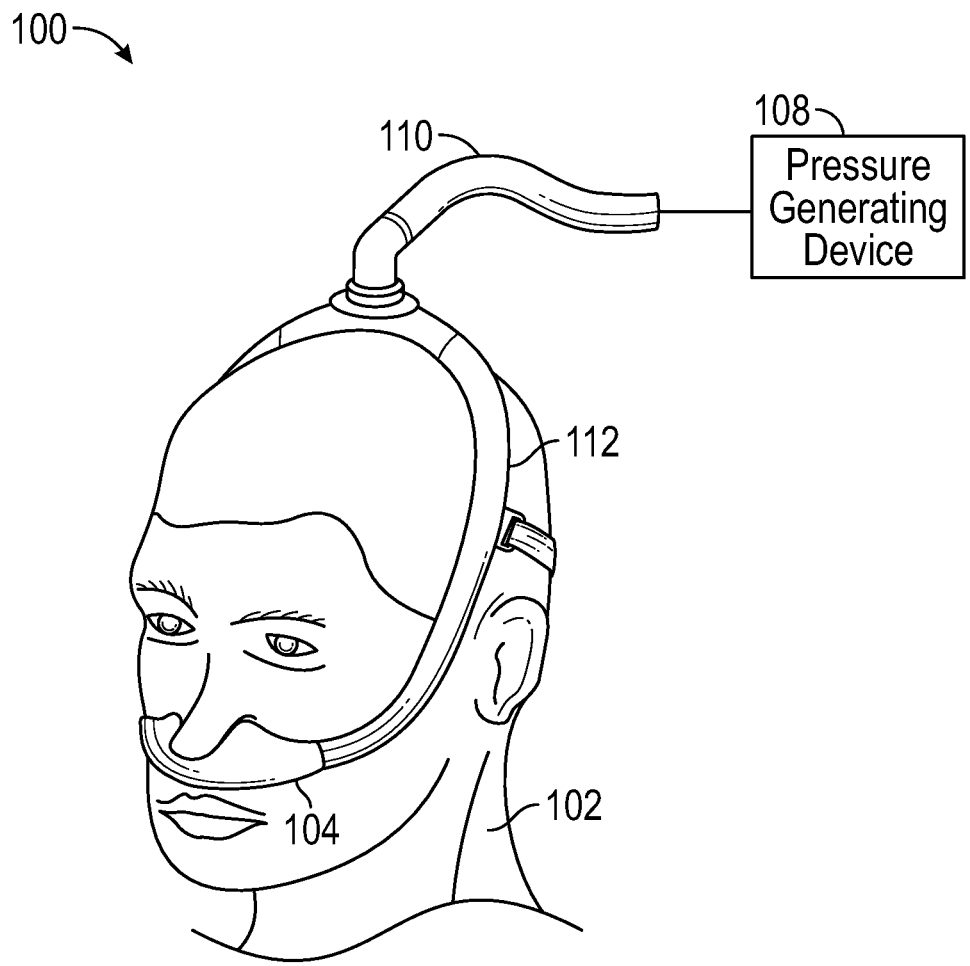
FIG. 6 is a schematic diagram of a pressure support system for providing a flow of treatment gas to the airway of a patient wherein a mask is selected for the patient using a 3D facial model that is generated according to the disclosed concept.

FIG. 6 is a schematic diagram of a pressure support system 100 for use in providing a flow of treatment gas to the airway of a patient 102. As seen in FIG. 6, system 100 employs a mask 104 that, as described herein, is selected for patient 102 using a 3D model obtained according to the methodology of the disclosed concept. As seen in FIG. 6, pressure support system 2 includes a pressure generating device 108, a delivery conduit 110, a tubing assembly 112, and the mask 104. Mask 104 is fluidly coupled to pressure generating device 108 via delivery conduit 110 and tubing assembly 112. Pressure generating device 108 is structured to generate a flow of positive pressure breathing gas and may include, without limitation, ventilators, constant pressure support devices (such as a continuous positive airway pressure device, or a CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 110 is structured to communicate the flow of breathing gas from pressure generating device 108 to mask 104 through tubing assembly 112 (the breathing gas enters at the top of the head of patient 102). Delivery conduit 110, tubing assembly 112 and mask 104 are often collectively referred to as a patient circuit.

In the example embodiment shown in FIG. 6, mask 104 is a nasal cushion made of a soft, flexible material, such as, without limitation, silicone, an appropriately soft thermoplastic elastomer, a closed cell foam, or any combination of such materials. However, it is to be appreciated that the methodology described in further detail below may be used to identify any type of mask (e.g., a nasal mask, a nasal cradle mask, a nasal pillows mask, a nasal/oral mask, or a full face mask that covers the patient's face) that facilitates the delivery of the flow of breathing gas to the airway of a patient without varying from the scope of the present invention.

Figure 7:
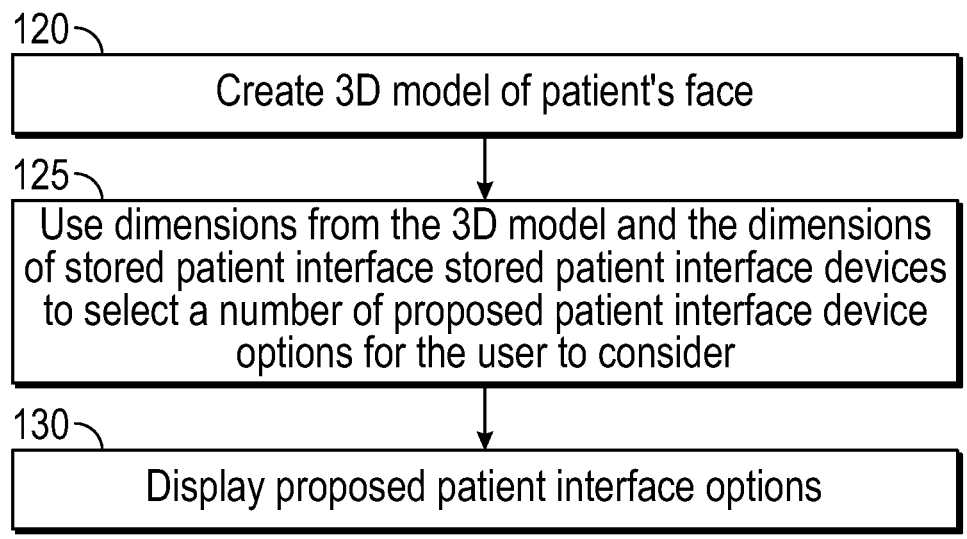
FIG. 7 is a flowchart showing a method of proposing patient interface device options for a patient for use in a system such as the pressure support system of FIG. 6 according to one particular exemplary embodiment of the disclosed concept.
Figure 8:
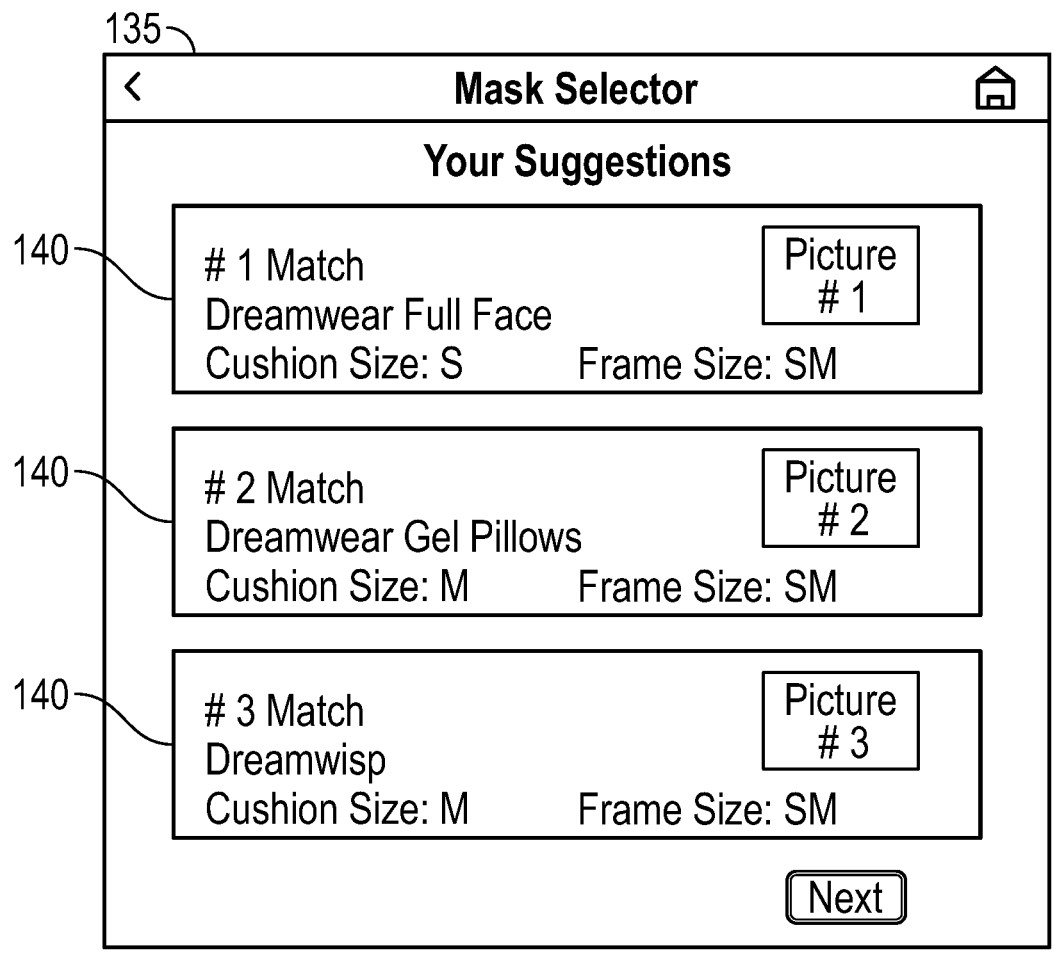
FIG. 8 is a schematic diagram of an exemplary screen that may be displayed on the display 8 of the apparatus of FIGS. 1-3 according to one particular exemplary embodiment of the disclosed concept.

FIG. 7 is a flowchart showing a method of proposing patient interface device options for a patient for use in a system such as pressure support system 100 according to one particular exemplary embodiment of the disclosed concept. In the exemplary embodiment, the method of FIG. 7 is implemented in application 16 of apparatus 2 (which may be downloaded from an "app store" or any other suitable source). The method begins at step 120, wherein a 3D model of the patient's face is generated using apparatus 2 according to the methodology of the disclosed concept as described herein. Next, at step 125, the dimensions from the generated 3D model and the dimensions of stored patient interface devices (e.g., masks, headgear, etc. of different sizes and/or types) are used to select a number of proposed patient interface device options for the patient to consider. Then, at step 130, the proposed patient interface options are displayed to the patient on display 8 of apparatus 2. For example, FIG. 8 shows an exemplary screen 135 that may be displayed on display 8 of apparatus 2. Screen 135 includes a number of patient interface device options 140 that have been chosen for the patient to consider in the manner described in connection with FIG. 7. The patient may then choose and purchase/acquire a desired patient interface device using any suitable method and/or source, including making the selection and purchase/acquisition with the downloaded application 16.

Thus, the present exemplary embodiment provides an improved method and apparatus for patient interface device selection that utilizes a 3D model of the patient's face that is generated in the more efficient and effective manner of the disclosed concept.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of creating a 3D model of a physical object, comprising:
adaptively and iteratively generating a number of disparity maps from image data representing a plurality of images of the physical object iteratively captured by a plurality of cameras having electrically adjustable focal lengths by varying at least one of the focal lengths of the plurality of cameras and a distance of the physical object from the plurality of cameras during capture of the images until one of the disparity maps is determined to have at least a threshold level of disparity; and
converting the one of the disparity maps into the 3D model, wherein the adaptively and iteratively generating the number of disparity maps comprises generating a first number of the disparity maps by varying the focal lengths of the plurality of cameras a number of times and determining that none of the first number of disparity maps has at least the threshold level of disparity, and responsive to determining that none of the first number of disparity maps has at least the threshold level of disparity providing an instruction to vary the distance of the physical object from the plurality of cameras during capture of the images, wherein the one of the disparity maps is extracted from a number of the images obtained after the distance is varied.

2. The method according to claim 1, wherein the determining that none of the first number of disparity maps has at least the threshold level of disparity comprises generating a disparity index for each of the first number of disparity maps, and wherein the determining that the one of the disparity maps has at least the threshold level of disparity comprises determining that a disparity index generated for the one of the disparity maps meets or exceeds a threshold value.

3. The method according to claim 2, wherein the disparity index for each of the first number of disparity maps is an aggregate of disparity scores of the images used to create the first number of disparity maps, and wherein the disparity index for the one of the disparity maps is an aggregate of disparity scores of the images used to create the one of the disparity maps.

4. A non-transitory computer readable medium storing one or more programs, including instructions, which when executed by a processor, causes the processor to perform the method of claim 1.

5. A method of proposing a number of articles for a subject, comprising:
   creating a 3D model of the subject according to the method of claim 1, wherein the subject is the physical object;
   selecting the number of articles based on dimensions from the 3D model and stored dimensions of the number of articles; and
   displaying the number of articles on a display of an electronic device.

6. The method according to claim 5, wherein the number of articles is a number of patient interface devices for use in a pressure support system.

7. An apparatus for creating a 3D model of a physical object, comprising:
   a plurality of cameras having electronically adjustable focal lengths; and
   a processing unit coupled to the plurality of cameras and structured and configured for:
      (i) adaptively and iteratively generating a number of disparity maps from image data representing a plurality of images of the physical object iteratively captured by the plurality of cameras by varying at least one of the focal lengths of the plurality of cameras and a distance of the physical object from the plurality of cameras during capture of the images until one of the disparity maps is determined to have at least a threshold level of disparity, and
      (ii) converting the one of the disparity maps into the 3D model, wherein the adaptively and iteratively generating the number of disparity maps comprises generating a first number of the disparity maps by varying the focal lengths of the plurality of cameras a number of times and determining that none of the first number of disparity maps has at least the threshold level of disparity, and responsive to determining that none of the first number of disparity maps has at least the threshold level of disparity providing an instruction to vary the distance of the physical object from the plurality of cameras during capture of the images, wherein the one of the disparity maps is extracted from a number of the images obtained after the distance is varied.

8. The apparatus according to claim 7, further comprising a display coupled to the processing unit, wherein the providing an instruction comprises displaying the instruction on the display.

9. The apparatus according to claim 7, wherein the determining that none of the first number of disparity maps has at least the threshold level of disparity comprises generating a disparity index for each of the first number of disparity maps, and wherein the determining that the one of the disparity maps has at least the threshold level of disparity comprises determining that a disparity index generated for the one of the disparity maps meets or exceeds a threshold value.

10. The apparatus according to claim 9, wherein the disparity index for each of the first number of disparity maps is an aggregate of disparity scores of the images used to create the first number of disparity maps, and wherein the disparity index for the one of the disparity maps is an aggregate of disparity scores of the images used to create the one of the disparity maps.

11. The apparatus according to claim 7, wherein the apparatus is a smartphone and wherein the plurality of cameras includes a first rear camera and a second rear camera of the smartphone.

\* \* \* \* \*